United States Patent
Fernandez Montequin et al.

(10) Patent No.: US 9,034,826 B2
(45) Date of Patent: *May 19, 2015

(54) USE OF EPIDERMAL GROWTH FACTOR FOR THE MORPHOFUNCTIONAL RESTORATION OF PERIPHERAL NERVES IN DIABETIC NEUROPATHY

(71) Applicant: Centro de Ingenieria Genetica y Biotecnologia, Ciudad de la Habana (CU)

(72) Inventors: Jose Ignacio Fernandez Montequin, Ciudad de la Habana (CU); Luis Saturnino Herrera Martinez, Ciudad de la Habana (CU); Jorge Amador Berlanga Acosta, Ciudad de la Habana (CU); Diana Garcia Del Barco Herrera, Ciudad Habana (CU); Danay Cibrian Vera, Ciudad de la Habana (CU); Gerardo Enrique Guillen Nieto, Ciudad de la Habana (CU); Raimundo Ubieta Gomez, Ciudad de la Habana (CU); Sonia Gonzalez Blanco, Ciudad de la Habana (CU); Vivian Maria Saez Martinez, Ciudad de la Habana (CU)

(73) Assignee: Centro de Ingenieria Genetica y Biotecnologia, Ciudad de la Habana (CU)

(*) Notice: Subject to any disclaimer, the term of this patent is extended or adjusted under 35 U.S.C. 154(b) by 0 days.

This patent is subject to a terminal disclaimer.

(21) Appl. No.: 14/140,849

(22) Filed: Dec. 26, 2013

(65) Prior Publication Data

US 2014/0105990 A1 Apr. 17, 2014

Related U.S. Application Data

(62) Division of application No. 12/443,837, filed as application No. PCT/CU2007/000018 on Oct. 1, 2007, now Pat. No. 8,642,552.

(30) Foreign Application Priority Data

Oct. 3, 2006 (CU) .................................... 20060192

(51) Int. Cl.
*A61P 25/02* (2006.01)
*A61K 38/18* (2006.01)
*A61K 9/16* (2006.01)
*C07K 14/485* (2006.01)

(52) U.S. Cl.
CPC ........... *A61K 38/1808* (2013.01); *C07K 14/485* (2013.01); *A61K 9/16* (2013.01); *Y10S 930/12* (2013.01)

(58) Field of Classification Search
None
See application file for complete search history.

(56) References Cited

U.S. PATENT DOCUMENTS 7,465,704 B2 12/2008 Berlanga Acosta et al.
2004/0043075 A1 3/2004 Ritter et al.

FOREIGN PATENT DOCUMENTS

| EP | 1723969 A1 | 11/2006 |
|---|---|---|
| JP | 2006152001 A | 6/2006 |
| KR | 20070060721 | 6/2007 |
| WO | WO9737002 A1 | 10/1997 |
| WO | WO9936513 A1 | 7/1999 |
| WO | WO0018413 A1 | 4/2000 |
| WO | WO0030675 A1 | 6/2000 |
| WO | WO0212335 A2 | 2/2002 |
| WO | WO02053167 A2 | 11/2002 |
| WO | WO2004096245 A2 | 11/2004 |
| WO | WO2006012707 A1 | 2/2006 |
| WO | WO2006079036 A2 | 7/2006 |

OTHER PUBLICATIONS

Bianchi, et al., "Interleukin-1 and Nociception in the Rat", Journal of Neuroscience Research, 53:645-650 (1998).
John, et al., "Multiple Sclerosis: Re-Expression of a Developmental Pathway that Restricts Oligodendrocyte Maturation", Nature Medicine, 8(10):1115-1121(2002).
Mehler, et al., "Postnatal Cerebral Cortical Multipotent Progenitors: Regulatory Mechanisms and Potential Role in the Development of Novel Neural Regenerative Strategies", Brain Pathology, 9(3):515-526(1999).
Wilson, et al., "Human Oligodendrocyte Precursor Cells in Vitro: Phenotypic Analysis and Differential Response to Growth Factors", GLIA, 44(2):153-165(2003).
Ye, et al., "Insulin-Like Growth Factor I Protects Oligodendrocytes from Tumor Necrosis Factor-α-Induced Injury", Endocrinology, 140(7):3063-3072(1999).
Ito, et al., "Collapse and Restoration of MHC Class-I-Dependent Immune Privilege", American Journal of Pathology, 164(2):623-634(2004).

(Continued)

*Primary Examiner* — Zachary Howard
(74) *Attorney, Agent, or Firm* — Hoffmann & Baron, LLP

(57) ABSTRACT

The present invention is relevant to human medicine, and, in particular, to the use of Epidermal Growth Factor (EGF) in a pharmaceutical composition, said composition is administered through infiltration at the periphery of nerve trunks and/or ganglia, for the morphofunctional restoration of peripheral nerves in painful, sensory-motor neuropathy, as well as ischemic neuritis. It is also relevant to an EGF containing composition, where this molecule can be formulated together with anesthetic or analgesic drugs, or encapsulated in microspheres, and their use for the morphofunctional restoration of peripheral nerves in painful, sensory-motor neuropathy, as well as in ischemic neuritis.

8 Claims, 1 Drawing Sheet

(56) References Cited

OTHER PUBLICATIONS

Li, et al., "Chronic Relapsing Experimental Autoimmune Encephalomyelitis: Effects of Insulin-Like Growth Factor-I Treatment on Clinical Deficits, Lesion Severity, Glial Responses, and Blood Brain Barrier Defects", Journal of Neuropathology and Experimental Neurology, 57(5):426-438(1998).

Martins, et al., "GH-releasing Peptide (GHRP-6)-Induced ACTH Release in Patients with Addison's Disease: Effect of Glucocorticoid Withdrawal", J. Endocrinaol. Invest., 26(2):143-147(2003).

Oishi et al., "Steroid Therapy for Multiple Sclerosis", Nippon Rinsho, 61(8):1361-1366(2003).

Thorne, et al., "Diffusion of Epidermal Growth Factor in Rat Brain Extracellular Space Measured by Integrative Optical Imaging", J. Neurophysiology, 92(6):3471-3481(2004).

Crang et al., "The Remyelinating Potential and In Vitro Differentiation of MOG-expressing Oligodendrocyte Precursors Isolated from the Adult Rat CNS", European Journal of Neuroscience, 20(6):1445-1460(2004).

Wang et al., "Infusion of Epidermal Growth Factor and Basic Fibroblast Growth Factor into the Striatum of Parkinsonian Rates Leads to In Vitro Proliferation and Differentiation of Adult Neural Progenitor Cells", Neuroscience Letter, 364(3):154-158(2004).

Gotter, et al., "Medullary Epithelial Cells of the Human Thymus Express a Highly Diverse Selection of Tissue-Specific Genes Colocalized in Chromosomal Clusters", Journal of Experimental Medicine, 199(2):155-166(2004).

Mathis et al., "Back to Central Tolerance", Immunity, 20:509-516(2004).

Anderson et al., "Profection of an Immunological Self Shadow Within the Thymus by the Aire Protein", Science, 298:1395-1400(2002).

Sakaguchi et al., "Naurally Arising CD4+ Regulatory T Cells for Immunological Self-Tolerance and Negative Control of Immune Responses", Annual Review of Immunology, 22:531-562(2004).

Frago et al., "Growth Hormone (GH) and GH-Releasing Peptide-6 Increase Brain Insulin-Like Growth Factor-I Expression and Activate Intracellular Signaling Pathways Involved in Neuroprotection", Endocrinology, 143:10:4113-4122(2002).

Harvey et al., "Neural Growth Hormone: An Update", Journal of Molecular Neuroscience:MN, 20:1:1-14(2003).

Schneider et al., "Central Effects of the Somatotropic System", European Journal of Endocrinology, 149:5:377-392 (2003).

Plata-Salaman, C.R., "Epidermal Growth Factor and the Nervous System", Peptides, Elsevier, Amsterdam, US, 12:3:653-663(1991).

Knapp et al., "Epidermal Growth Factor Promotes Oligodendrocyte Process Formation and Regrowth After Injury", Experimental Cell Research, 296:2:135-144(2004).

Raineteau et al., "Neurogenesis in Hippocampal Slice Cultures", Molecular and Cellular Neuroscience, 26:2:241-250 (2004).

Kuhn et al., "Epidermal Growth Factor and Fibroblast Growth Factor-2 Have Different Effects on Neural Progenitors in the Adult Rat Brain", Journal of Neuroscience, 17:15:5820-5829(1997).

Arsenijevic et al., "Insulin-Like Growth Factor-I is a Differentiation Factor for Postmitotic CNS Stem Cell-Derived Neural Precursors: Distinct Actions from those of Brain-Derived Neurotrophic Factor", Journal of Neuroscience, 18:6:2118-2128(1998).

Rom et al., "Glutamate Receptor Antagonists and Growth Factors Modulate Dentate Granule Cell Neurogenesis in Organotypic, Rat Hippocampal Slice Cultures", Brain Research, 1051:1-2:35-49(2005).

Ulbrecht et al., Clinical Infectious Diseases, 39(2): S73-82 (2004).

Acosta et al., International Wound Journal, 3(3): 232-239 (2006).

Aring et al, Am Fam Physician, 71:2123-2128 (2005).

USE OF EPIDERMAL GROWTH FACTOR FOR THE MORPHOFUNCTIONAL RESTORATION OF PERIPHERAL NERVES IN DIABETIC NEUROPATHY

CROSS-REFERENCE TO RELATED APPLICATIONS

This application is a divisional of U.S. application Ser. No. 12/443,837, filed on Apr. 1, 2009, which is a National Phase application of International Application No. PCT/CU2007/000018 filed Oct. 1, 2007, which claims priority based on Cuban Application No. 20060192 filed Oct. 3, 2006, which are incorporated herein by reference.

TECHNICAL FIELD

The present invention is pertinent to medical or experimental applications of a pharmaceutical composition comprising Epidermal Growth Factor (EGF), preferably administered by infiltration in the periphery of nerve trunks and/or ganglia, to prevent or correct any of the clinical manifestations of diabetic neuropathy, and the manifestations of ischemic neuritis. Said formulation can be also administered locally, to in distal regions of the extremities or on the base of amputated limbs experiencing neuropathic pain.

PREVIOUS ART

Insufficient levels of glucose in blood and other diabetes related factors can alter the is nervous fibers in any part of the body generating a group of disorders with specific characteristics, depending on the affected nerves. These disorders are altogether named diabetic neuropathy, and at least three major types have been described: (1) sensory-motor neuropathy (most typical and frequent form), (2) autonomic neuropathy and (3) mononeuropathy (Sadikot S M, Nigam A, Das S, et al. (2004). The burden of diabetes and impaired glucose tolerance in India using the WHO 1999 criteria: prevalence of diabetes in India study (PODIS). *Diabetes Res Clin Pract*, 66, 301-7).

Although the precise mechanisms behind these disorders are not completely understood, it is known that the nervous fiber is structurally modified by the accumulation of substances derived from the exacerbated metabolism of glucose, which leads to the loss of the myelin sheath in the nervous fibers. The lost of this protective sheath implies a delay in the capacity to transmit the nervous impulse, either in reception, transmission of motor orders or any other kind of signals. In addition to this direct mechanism, the blood vessels irrigating the nerves can suffer obstructions by events that are common to other chronic complications of diabetes (Ashok S, Ramu M, Deepa R, et al. (2002). Prevalence of neuropathy in type 2 diabetes patients attending diabetes center in South India. *J Assoc Physicians India*, 50, 546-50).

As is common in diabetes, the initial phases of diabetic neuropathy are generally asymptomatic, even for years, and until now there is no way to anticipate their insidious clinical course. When the doctor suspect of a sensory-motor diabetic neuropathy he can confirm the diagnosis by conducting a test to assess the velocity of nervous conduction. This test consist in determine the velocity of transmission of small electrical currents through the selected nervous.

In the more frequent form of diabetic neuropathy, the sensory-motor neuropathy, the initial symptoms include lost of sensibility, incorrect perception of tactile sensations and, in certain cases, exquisite pain after minimal skin grazes. Normally, this occurs firstly in feet and hands and mostly during the night. When the affected nerves are in charge of the digestive motility, slow digestive process or alterations of the intestinal rhythm (diarrhea and/or constipation) can take place. Sometimes the diabetic neuropathy affects the cardiovascular system control, producing syncope or hypotension if the patients get up suddenly (Levitt N S, Stansberry K B, Wychanck S, et al. (1996). Natural progression of autonomic neuropathy and autonomic function tests in a cohort of IDDM. *Diabetes Care*, 19, 751-54).

Diabetic mono-neuropathy can affects virtually any isolated nerve, originating paralysis in one side of the face, alteration of the eye movements, paralysis and/or pain in a concrete anatomical location.

Peripheral neuropathy can affect the cranial nerves or those of the spinal cord and its ramifications and is a type of neuropathy (nervous lesion) which tends to develop by stages. At the beginning there is pain and intermittent tangling in the extremities, particularly in the feet; while in more advance stages the pain is more intense and constant. Finally, a painless neuropathy is developed when nervous deterioration is massive (Oh S J. (1993). Clinical electromyography: nerve conduction studies. In: Nerve conduction in polyneuropathies. Baltimore: Williams and Wilkins, p: 579-91).

One of the more severe consequences of diabetic neuropathy is the associated pain, which is sometimes of high intensity and does not respond to standard therapeutic procedures. Pharmacological and clinical treatments have been used without much success. The former have been mostly indicated in combination with analgesics, non steroidal anti-inflammatories, anticonvulsants such as carbamazepine and fentolamine, tricyclic anti-depressives, and local anesthetics, which can penetrate even to reach the blocked fibers. Anticonvulsants have been recently used to treat diabetic neuropathy associated pain. Among them, the most recently introduced to treat pain is gabapentin. Neurochemically, gabapentin increase Gamma-amino butyric acid (GABA) bioavailability, inhibit GAT-1 carrier, which in turns reduce the recapture of GABA; decrease the synthesis and release of biogenic amines such as noradrenalin, dopamine and 5-OH-triptamine; and induce the release of encephalin type opium peptides involved in pain modulation. (Didangelos T P, Karamitsos D T, Athyros V G, et al. (1998). Effect of Aldose reductase inhibition on cardiovascular reflex tests in patients with definite diabetic autonomic neuropathy. *J Diabetes Complications*, 12, 201-7).

In patients with painful neuropathy and lack of response to the treatment, transcutaneous electronic stimulation has been used in such a way that, by applying programmed, low intensity voltages, the transmission of the pain through the affected nerves has been prevented.

Painful diabetic neuropathy has been divided in chronic and acute forms. The acute form is typically observed during the first three years after diagnosis; it begins and is ends spontaneously. The chronic form is present in persons suffering the disease for 8 or 9 years as average. It begins slowly and persists for years with multiple relapses. Cranial neuropathies can affect vision and cause pain in the eye.

The symptoms of the disease are, in general, drowsiness, tingling, lost of sensitivity in some parts of the body, diarrhea or constipation, lost of bladder control, impotency, ptosis of the face, the eyelids and/or the mouth. It can also cause changes of the vision, dizziness, swelling difficulties, language alterations and muscular contractions. Those symptoms vary depending upon the affected nerve or nerves and, in general, develop gradually.

The loss of sensitivity associated to diabetic neuropathy increments the risk of lesions. Small infections can progress until become ulcers and require amputation. Besides, damage in motor nerves can lead to decomposition and muscular disequilibrium. In other words, neuropathy is perhaps the principal cause of legs and feet amputation in this disease.

The objectives of diabetic neuropathy treatment are the prevention of the progress and reduction of symptoms of the disease. The strict control of glucose is important to avoid that progress. No specific treatment capable of prevent, retard or revert the alteration in nerve fibers in diabetic neuropathy is currently available. No drug capable of repair the nervous damage has been approved, but several of them are presently under study. Complex B vitamins are, possibly, the most used drugs for all forms of neuropathy. Although these drugs relieve some symptoms, they are no more than a palliative. Other therapeutic alternative recently used is the application of lipoic acid by intravenous route, based on its antioxidant properties. (Ziegler D, Hanefeld M, Ruhnau K J, et al. (1999). Treatment of symptomatic diabetic polyneuropathy with the antioxidant alpha-lipoic acid: a 7 month multicenter randomized controlled trial (ALADIN III study). ALADIN III study group. Alpha-lipoic acid in diabetic neuropathy. *Diabetes Care,* 22, 1296-301). Other assays have been carried out to introduce oral treatment with Acetyl L-carnitine, a compound showing discrete influence on the small sensory fibers.

The only therapeutic procedure with a pathogenic basis for peripheral diabetic neuropathy involves the use of aldose-reductase inhibitors. Its activity is based on the role of aldose-reductase in the structural and functional metabolic disorders, induced by hyperglycemia in the nerves of the diabetic organism. So far Sorbinil, which is effective in improving the motor conduction speed in diabetic persons with neuropathy, was evaluated in clinical trials, but it was withdrew from the market due to toxic effects. Statil showed encouraging results in animals, but these results could not been corroborated in humans. In general aldose-reductase inhibitors are very toxic.

Considerable optimism raised the introduction of Nerve Growth Factor (NGF) and other growth factors in clinic. In an assay with 250 patients with small fibers (C fibers) neuropathy, pain release and increasing capacity to detect hot stimuli were documented. However, in two subsequent assays with higher number of patients, treatment with NGF did not showed any benefit (Vinik A I. (1999). Treatment of diabetic polyneuropathy (DPN) with recombinant human nerve growth factor (rh NGF). *Diabetes,* 48, A54-5).

Gene therapy with Vascular Endothelial Growth Factor (VEGF) has been extensively evaluated in animals, showing improvement in the conduction of nerve impulses and in the density of blood vessels draining the nerve. However, this and other approaches with additional neurotrophic agents have been unable to halt the progression to diabetic neuropathy in clinical trials, despite previous positive results in animals. (Schratzberger P, Walter D H, Rittig K, et al. (2001). Reversal of experimental diabetic neuropathy by VEGF gene transfer. *J Clin Invest,* 107, 1083-92). To reduce the symptoms topical treatment with capsaicin or oral drugs such as amitriptyline, gabapentin and carbamazepine are recommended.

The pathogenic mechanisms of diabetic neuropathy are not well understood. Current treatment release pain and can control part of the associated symptoms but the process is generally progressive. The worst part is that a specific drug for this disease does not seem to be available in the next future.

SUMMARY OF THE INVENTION

This invention contributes to solve the above mentioned problem by using EGF in a pharmaceutical composition which is administered through infiltration in the periphery of nerve trunks and/or ganglia, for the morphofunctional restoration of peripheral nerves in painful, sensory-motor neuropathy, as well as in ischemic to neuritis.

The diabetes associated alterations of peripheral nerves are complex and probably involve a variety of causes. The two main pathogenic mechanisms are 1) the theory of sorbitol accumulation leading to a series of biochemical anomalies which, in the long run, cause structural alterations in peripheral nerves. 2) Structural and is functional damage of endoneurial microvessels, originating changes in the nervous fibers triggered by hypoxia or ischemia. Other mechanisms of generation of diabetic neuropathy are the modulation of enzymes production, the activation of the complement system, the accumulation de proteins with high affinity for heavy metals such as iron and copper, and the diminution of neurotrophic factors. Another element that has been emphatically claimed is the accumulation of peroxidation and nitrosilation products. A reduction in endoneurial oxygen tension has been observed in the nerves of diabetic patients suffering from neuropathy. All these events lead to a high level of apoptosis and cell death in neural structures. This is the reason why diabetic neuropathy is characterized by the lost of functional units at the level of myelinated nerve fibers and a significant reduction in nerve conduction velocity (NCV). Peripheral polyneuropathy is characterized by the presence of pain, which is related to alpha and C fibers dysfunction.

In general, the composition of the present invention is applied by local infiltration, placing it near to nerve trunks and/or ganglia, distal pain zones of the legs before or after amputation, and in those cases where the expert in the art appreciates damage in the C fibers. The treatment with the present composition for several weeks has shown to be able to eliminate neuropathic pain; to moderate non autonomic disorders; and to restore peripheral sensibility to pressure and temperature.

After three systemic injections, or local infiltrations at the periphery of the nerve trunks, of the pharmaceutical composition in diabetic animals we have detected:

1. Improvement in the integrity of the myelin sheath of the sciatic nerve.
2. Reductions in axon edema.
3. Preservation of axonal neurofilaments
4. Integrity of the vasa nervorum.
5. Diminution of endoneurial collagenization.
6. Normalization of conduction velocity of motor fibers The composition is released slowly near to the structure of interest in a volume of 1 to 5 milliliters. The frequency of infiltration in nerve trunks and ganglia can fluctuate between one and three times a week. The treatment with the composition described in this invention can be or not associated with inhibitors of aldose reductase, aminoguanidine, oral or parenteral hypoglycemics, insulin, stimulants of peripheral sensitivity to insulin, glucagon like peptides, vitamin therapy, agonists or amplifiers of GABA system, endorphin precursors, anti-oxidants, fatty acids or their precursors, individual or combined therapy with analgesics, tricyclic anti-depressives and anti-inflammatory drugs. The number of applications administered to a patient varies according to the severity of the clinical symptoms of the patient. Several cycles of treatment are required if the symptoms reappear.

One particular embodiment of the present invention is the use of EGF to prepare formulations administered by infiltration in the periphery of nerve trunks and/or ganglia for the morphofunctional restoration of peripheral nerves in sensorymotor neuropathy, when the more important manifestations of this neuropathy affect the legs. In a preferred embodiment, the EGF used to prepare the pharmaceutical composition administered through infiltration in the periphery of nerves trunks and/or ganglia for the morphofunctional restoration of peripheral nerves, is the human recombinant EGF.

In another particular embodiment of the invention, the infiltration of the EGF containing pharmaceutical composition is made in the sciatic nerve.

An object of the present invention is an injectable pharmaceutical composition containing a combination of EGF and at least one local anesthetic or analgesic, administered through infiltration in the periphery of nerve trunks and/or ganglia, for the morphofunctional restoration of peripheral nerves in diabetic neuropathy. In a particular embodiment, said anesthetic is lidocaine, which contributes to relieve the pain caused by EGF infiltration. Moreover, the accompanying anesthetic present in the composition can be bupivacaine or novocaine, among others.

There is also part of the present invention, a composition in which EGF is administered through infiltration in the periphery of nerve trunks and/or ganglia, with the aid of controlled-release systems. In a preferred embodiment, said controlled-release system are microspheres made of lactic acid and glycolic acid, or polylactic acid copolymers, which bear the EGF.

Microspheres can offer several advantages, being the most common a reduction in the frequency of administration. The present invention provides a technical solution to the lack of an available drug specific for the treatment of diabetic neuropathy. However, treatment with EGF containing compositions, where this molecule is not bound to microspheres, requires the application of the corresponding doses of the drug at least twice a week. Taking into account this inconvenient, the use of a formulation for the slow and sustained release of EGF reduces the frequency of administration of the product, which is beneficial for the patient. The formulation based on microspheres has the following advantages:

Diminution in the frequency of administration, which leads to a better adherence to the treatment by the patient.

Increase in the therapeutic benefit due to the elimination of the fluctuations in the protein levels in serum.

Potential diminution of the total dose required for treatment due to a better performance of the administered dose.

Potential diminution of adverse effects due to a reduction in the amount of protein released in the body at the moment of the application.

DETAILED DESCRIPTION OF THE INVENTION/EXAMPLES

Example 1

Figure 1:
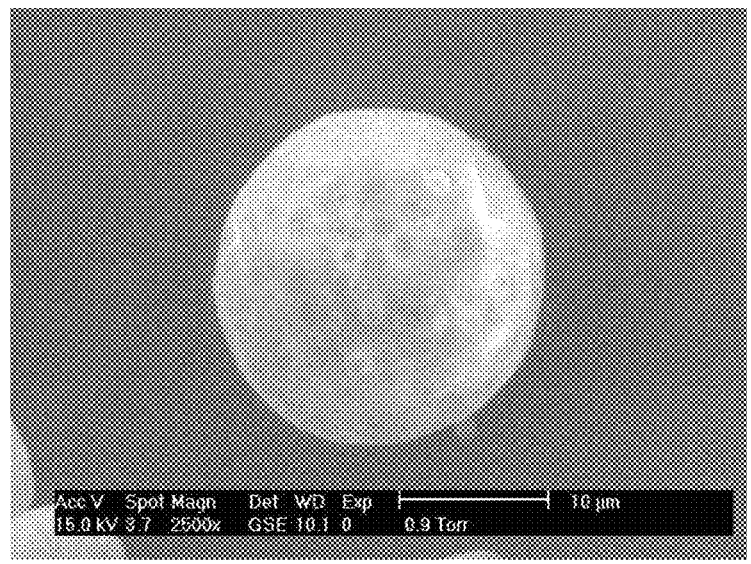
FIG. 1. Microphotography of an EGF loaded microsphere. The bar below the microphotography represents a length of 10 µm.

Preventive Effect of the Pharmaceutical Composition in the Instauration of Diabetic Neuropathy The aim of this study was to evaluate the neuro-protective effect of the EGF containing pharmaceutical composition in an animal model of Diabetes Mellitus. Firstly, it was necessary to establish the methodology of Diabetes Mellitus induction in Wistar rats by administering streptozotocin.

Male Wistar, with 200-250 grams of body weight, received a subcutaneous injection of streptozotocin, at 75 mg/kg in sodium citrate buffer. Water was then replaced by a 10% sucrose solution during the next 24 h, to prevent deaths caused by hypoglycemia. Glucose levels in blood were monitored every morning during the next 72 hours after the injection. Only animals with sustained glucose values above 15 mmol/L were used. Rats were housing at 4 per cage and fed in the conventional way. A concurrent group of other 80 rats received citrate buffer without streptozotocin and was handled in a similar fashion to the diabetic group. The average value for glycemia during the 72 hours in this group was 5.87 mmol/L.

To study the effect of EGF containing pharmaceutical composition in the prevention of diabetic neuropathy the following experimental design was used with 10 rats per each one of the groups:

Control group—A group of diabetic rats receiving saline three times a week in 1 ml by intraperitoneal route.

Treatment group 1—A group of diabetic rats receiving EGF containing pharmaceutical composition once weekly in 1 ml by intraperitoneal route.

Treatment group 4—A group of diabetic rats receiving EGF containing pharmaceutical composition three times a week in 1 ml by intraperitoneal route All treatments were conducted during 8 weeks, starting one week after streptozotocin injection. The composition used contained 75 µg of human recombinant EGF/ml. Several types of observations were conducted in the animals under study:

(1) Determination of Nociceptive Threshold (NCT). Pain Test.

The pain test, by application of an increasing pressure in the tail, was carried out at days 28 and 56 after initiation of the treatment, using 10 animals per each one of the experimental groups. NCT, expressed in grams, was determined by using an Ugo Basile type analgesimeter to apply a gradually increasing pressure to the tail of the animals until they developed a withdrawal reflex. In human diabetic neuropathy the nociceptive threshold is reduced. Table 1 shows the results of NCT measured at day 28.

TABLE 1

Results of NCT test (28 days).

| Experimental group | NCT* (grams) |
|---|---|
| Saline control | 120 ± 11 |
| Treatment group 1 | 125 ± 18 |
| Treatment group 3 | 123 ± 16 |
| Non diabetic rats | 128 ± 9 |

*Data expressed as the average and standard deviation.

No changes in the nociceptive pattern of the animals are detected after 28 days of disease evolution. This suggests that the clinical form of hyperesthesia has not been installed yet. For this reason, an effect of the treatment can not be yet appreciated at this time point. Results of the examination at day 56 are shown in Table 2.

As the results demonstrated, two months after diabetes induction it is possible to appreciate the effect of peripheral diabetic neuropathy in the animals. A reduction in the pain sensitivity threshold was detected at this experimental point. There is also remarkable the difference between the group of diabetic rats receiving saline during two months and the group receiving treatment with the EGF containing composition three times a week.

TABLE 2

Results of NCT test (56 days).

| Experimental group | NCT (grams) |
|---|---|
| Saline control | 80 ± 19** |
| Treatment group 1 | 91 ± 14* |
| Treatment group 3 | 121 ± 22 |
| Non diabetic rats | 123 ± 6 |

Significant differences between the diabetic group treated with saline and the group receiving treatment 3, as well as with the group of non diabetic rats, were observed (**$p<0.01$ ANOVA with Bonferroni correction). There were also significant differences between the group of treatment 1 and groups of treatment 3 and healthy animals. The finding that treated animals in general showed more tolerance to pain suggests that the treatment with EGF containing composition did prevent the deterioration of sensory fibers.

(2) Determination of the Conduction Velocity of the Impulse by Sensory Fibers.

To assess the protective effect of the EGF containing pharmaceutical composition on sensory and motor fibers, the conduction velocity of an electric impulse was measured at day 60 after initiation of treatment. Fifteen animals were used in each experimental group. In diabetic neuropathy conduction velocity is generally diminished.

Distal supra-maximal stimulation in the sciatic-tibial route using bipolar electrodes is was used to study motor conduction. Determination of the conduction velocity in the sensory routes was carried out by applying a stimulus at a proximal point in the tail and measure it 3 cm away. The results of this study at day 60 are shown in Table 3.

TABLE 3

Motor conduction velocity (MCV) at day 60.

| Experimental group | MCV (m/s) |
|---|---|
| Saline control | 34 ± 18** |
| Treatment group 1 | 45 ± 13* |
| Treatment group 3 | 56 ± 11 |
| Non diabetic rats | 60 ± 8 |

Significant differences between the diabetic group treated with saline and the group receiving treatment 3, as well as with the group of non diabetic rats, were observed (**$p<0.01$ ANOVA with Bonferroni correction). There were also significant differences between the group of treatment 1 and groups of treatment 3 and healthy animals (*$p<0.05$); and between treatment group 1 and control diabetic animals receiving saline.

Note the positive effect of the composition, in particular in the group receiving three applications weekly. Values of conduction in motor fibers are very similar to those in healthy animals. Although still with statistical difference with the group of non diabetic animals, rats in the group receiving treatment 1 also improved the conduction velocity. The results of the study of sensory conduction velocity (SCV) at day 60 are shown in Table 4.

TABLE 4

Sensitive conduction velocity (SCV) at day 60.

| Experimental group | SCV m/s |
|---|---|
| Saline control | 31 ± 7** |
| Treatment group 1 | 38 ± 6* |
| Treatment group 3 | 44 ± 9 |
| Non diabetic rats | 56 ± 3 |

Significant differences between the diabetic group treated with saline and the group receiving treatment 3, as well as with the group of non diabetic rats, were observed (**$p<0.01$ ANOVA with Bonferroni correction). There were also significant differences between the group of treatment 1 and groups of treatment 3 and healthy animals (*$p<0.05$); No statistical differences were detected between treatment group 1 and control diabetic animals receiving saline. This study demonstrates the effect of the EGF containing pharmaceutical composition to preserve the functional integrity of animals when administered three times a week.

(3) Influence of the Composition in the Integrity of Blood Perfusion of a Peripheral Nerve.

The right sciatic nerve of rats was used as a model. Ten animals were included for each one of the experimental groups. A similar number of non diabetic rats were used to calculate the reference values. A Laser Doppler Perfusion Imaging (LDPI) system was used. Data of perfusion in peripheral tissues to the nerve were programmed as zero values. Control animals received saline during two months before the measurement. All determinations were done under the same conditions of anesthesia and environmental conditions. They are reflected in Table 5.

TABLE 5

Results of the study conducted with the Laser Doppler Perfusion Imaging System.

| Experimental group | LDPI Units |
|---|---|
| Saline control | 525.5 ± 88.8** |
| Treatment group 1 | 653.4 ± 41.9** |
| Treatment group 3 | 988.7 ± 80.3 |
| Non diabetic rats | 1301.7 ± 112.2 |

Significant differences between the diabetic group treated with saline and the group receiving the therapeutic composition once a week, both treatments during two months; and also with those receiving the therapeutic composition three times a week (**p<0.01 ANOVA with Bonferroni correction) were observed. No statistical differences were detected between the latter group and the values from healthy non diabetic rats.

(4) Post-Mortem Determinations and Characterizations.

Histomorphometric Study.

Once the treatment was concluded, animals were sacrificed at day 70 after induction of diabetes, 10 days after the last dose was given, and the analysis described above is was completed. Animals were sacrificed by an overdose of anesthesia and perfused with saline buffer pH 7.4. A total of ten animals per experimental group were included for histomorphometric studies, and an equivalent number of rats were used for biochemical determinations. In both systems the sciatic nerves from both limbs were dissected; fragments were kept at −70° C. until processed. The samples taken for histological and/or histomorphometric studies were stained with hematoxilin/eosin and toluidine blue. At least five fragments of the same nerve were quantitatively studied using MADIP program. The fragments were included in blocks of celloidine and gelatin, and those blocks were horizontal and transversally sliced. The following histological indicators were evaluated:

Total number of blood vessels (in epineural/perineural) in 10 microscopic fields using 10× as constant magnification in longitudinal cuts of the nerve.

Percentage of demyelinated fibers. Evaluated by averaging the values per microscopic field (×20, at least five fields).

Percentage of myelin or non-myelin fibers with lesions (dilated or distorted) per microscopic field (×20, at least five fields).

Percentage of endoneurial collagenization (moderated: 25 to 50%; severe: more than 50% of the endoneurial area in transversal slices, and at least three different sections.

The results of this study are shown in Table 6.

over, statistical differences were also found when the saline group and the group receiving treatment 1 were compared (p=0.031). There were also statistical differences (p=0.014) when saline group was compared with the group receiving treatment 3. Results were analyzed by ANOVA with Bonferroni correction. The percentages were compared with Fisher exact test.

Statistically significant differences between treatment groups for the three parameters were found: Percentage of demyelinated fibers, Percentage of fibers with lesions and Percentage of collagenized areas. Statistical difference between the group of insulin treated diabetic mice and animals receiving treatment 3 were detected (p<0.05).

Partial Conclusions—

Treatment with the EGF containing composition, three times a week, for two months, was able to prevent the demyelinization process, to reduce significantly the morphological deterioration of sciatic nerve fibers and, consequently, to prevent endoneurial collagenization. In a similar way, sustained treatment with this composition avoids significantly atrophy and degeneration of blood vessels nurturing the nerve. All these findings are in agreement with the functionally tests conducted regarding sensory and motor stimuli conduction, and the perfusion study with the Laser Doppler system.

(5) Biochemical Characterization of Nerve Fragments.

Ten animals per experimental group were used to conduct biochemical determinations in the fragments of sciatic nerve collected. The biochemical parameters studied were the following:

Redox Profile:

Activity of total Superoxide Dismutase enzyme (tSOD).

Activity of catalase enzyme.

TABLE 6

Morphometric study conducted on fragments of the Sciatic nerve.

| Experimental group | Number of blood vessels | % of demyelinated fibers | % of fibers with lesions | % of collagenized area |
|---|---|---|---|---|
| Saline control | 87.65 ± 17.8 | 64.77 ± 19.72 | 81.5 ± 9.73 | 58.93 ± 28 |
| Treatment group 1 | 111.33 ± 14.5 | 51.2 ± 17.94 | 60.12 ± 11 | 42.69 ± 14.71 |
| Treatment group 3 | 158.6 ± 26.12 | 35.56 ± 12.18 | 41.38 ± 10.26 | 13.45 ± 11.82 |
| Non diabetic rats | 194.42 ± 43.81 | 0 | 0 | 0 |

Statistically significant differences in the number of blood vessels between the group of saline treated diabetic animals and healthy control rats were documented (p=0.0023). More- Intra-axonal accumulation of total hydroperoxides (HPT).

Intra-axonal accumulation of malonyldialdehyde (MDA).

The results of this study are shown in Table 7.

TABLE 7

Characterization of the Redox state in fragments from the sciatic nerve.

| Experimental Groups | tSOD[a,b] | Catalase | HPT[c] | MDA |
|---|---|---|---|---|
| Non diabetic rats | 2267.05 ± 202.9 | 26.40 ± 5.95 | 18.66 ± 1.43 | 0.06 ± 0.01 |
| Saline Group | 433.55 ± 95.21** | 440.26 ± 52.19** | 208.62 ± 11.3** | 0.32 ± 0.02** |
| Treatment group 1 | 958.17 ± 244.61* | 274.60 ± 52.3* | 143.05 ± 1.98* | 0.24 ± 0.04* |
| Treatment group 3 | 2102.83 ± 112.67 | 37.62 ± 8.13 | 25.15 ± 1.81 | 0.08 ± 0.02 |

[a]Values are expressed as the average and standard deviation.
[b]Enzymes expressed as units per milligram, of protein per minute.
[c]HPT and MDA in nmol/mg of protein.

Significant differences between placebo treated diabetic animals and those treated three times a week with the EGF containing composition were observed (** p=0.0001). There were also differences between groups treated with the EGF containing formulation once a week and three times a week, and also when compared with non diabetic animals (*p=0.003). No differences between healthy animals and those treated three times a week were found according to a two tails T to Student.

Because glucose accumulation contribute through several biochemical mechanisms to increase the level of lipid peroxidation, and. in turns, to the accumulation within the tissues of advance glycosylation endproducts (AGE), it is indispensable to evaluate markers related with this process. As demonstrated by the results shown in Table 7, is treatment with the assayed pharmaceutical composition reduces significantly the accumulation of metabolites indicative of peroxidation processes, and depends upon the frequency of application. In parallel, the treatment is able to prevent the diminution of Superoxide Dismutase.

(6) Lipoprotein Lipase (LPL) Enzymatic Activity in Sciatic Nerve Fragments.

Fragments of the nerve from each animal were incubated together with 3 µg/ml heparin in Krebs-Ringer buffer at 37° C. for 50 minutes. Aliquots from these samples were then incubated in the presence of [$^{14}$C] triolein-phosphatidylcholine. $^{14}$C labeled fatty acids were quantified by the classic methods. LPL activity was expressed in nanomoles of released fatty acids (RFA) per minute and gram of tissue. Results are shown in Table 8.

TABLE 8

LPL activity in the sciatic nerve.

| Experimental Groups | LPL (nmoles RFA/min/g) |
|---|---|
| Non diabetic rats | 6.18 ± 1.05 |
| Saline control | 2.24 ± 0.97** |
| Treatment group 1 | 3.75 ± 2.2* |
| Treatment group 3 | 5.41 ± 1.83 |

Significant differences between saline treated diabetic rats and the group receiving treatment 3, as well as with the group of non diabetic rats were found (**p<0.01, ANOVA and Tukey test). There were also differences (*p<0.05) between the group of treatment 1 and the control animals. No statistically significant differences were found between treatment 3 and non diabetic animals.

The present analysis shows that treatment with the EGF containing composition guaranties the preservation of LPL enzymatic activity, which in turns improves the capacity of the nerve to synthesize myelin, due to the relevant contribution of phospholipids to this function.

Example 2

Effect of the Pharmaceutical Composition in the Reversion of Established Diabetic Neuropathy The aim of this study was to evaluate the neurorestoration effect of the pharmaceutical composition. Male Wistar rats between 200-250 grams of body is weight received a subcutaneous injection of streptozotocin at 75 mg/kg in sodium citrate buffer, and were allowed to evolve until 120 days after disease induction. All rats used in this experiment had shown sustained glucose levels above 15 mmol/L. Animals were handled and fed as previously described. A concurrent control group was set, where animals received saline instead of streptozotocin. Animals were observed for three months after streptozotocin challenge. After this period an electrophysiological characterization of all rats were done and animals were split in two random treatment groups:

Group I. Animals received saline (1 ml), 3 days a week, by intraperitoneal route.

Group II. Animals received the pharmaceutical composition with 100 µg of EGF in 1 ml, 3 days a week, by intraperitoneal route.

A group of at least 10 healthy, non diabetic rats from the same litter was included as a reference for physiological values in non diabetic animals. The results of the neurophysiologic characterization of the animals before treatment initiation are shown in Table 9. The methodology employed in these explorations has been previously described.

TABLE 9

Neurophysiologic characterization of animals before treatment initiation.

| Studied Parameter | Diabetic | Non diabetic |
|---|---|---|
| Nociceptive Threshold | 55 ± 5 grams | 115 ± 15 grams |
| Motor Conduction Velocity | 20.53 ± 8.44 m/s | 66.18 ± 4.32 m/s |
| Sensory Conduction Velocity | 26.88 ± 13.27 m/s | 69.94 ± 11.8 m/s |
| Blood irrigation to the nerve | 480.61 ± 65.92 LDPI | 1413.8 ± 73.41 LDPI |

(1) Determination of Nociceptive Threshold (NCT). Pain Test.

The pain test, consisting of the application of a gradually increasing pressure in the tail, and the rest of the explorations described next, were carried out at day 120 after the induction of diabetes and after a month of treatment. At least 10 animals per each one of the experimental groups were used. NCT determination was conducted as previously described and the results are depicted in Table 10.

TABLE 10

Results of NCT test.

| Experimental group | UNC (grams) |
|---|---|
| Diabetic + Saline | 55 ± 10** |
| Diabetic + Treatment | 80 ± 5* |
| Non diabetic rats | 115 ± 10 |

Significant differences between the group of diabetic rats treated with saline and the group of rats receiving the treatment, as well as with the group of non diabetic rats were observed (**p<0.01 ANOVA and Bonferroni correction). There were also differences between treatment group and intact animals (* p<0.05).

The results demonstrate that three months after diabetes induction there is an increment in the progression of peripheral neuropathy, a reduction in the pain sensitivity threshold in more than 50% as compared with healthy animals. There is also noteworthy the difference observed between the group of diabetic rats and the group treated three times a week, during one month, with the pharmaceutical composition.

Treated animals, in general, showed higher tolerance to pain, a finding suggesting that treatment with the pharmaceutical composition corrected or restored in some way the sensory fibers.

(2) Determination of the Conduction Velocity of an Impulse Through Motor Fibers.

To check the effect of the pharmaceutical composition on the restoration of sensory and motor fibers the conduction velocity of an electric impulse was measured at day 120 after induction of diabetes, after treating the animals with the pharmaceutical composition or saline. Fifteen animals per experimental group were used. The is procedure followed was already described for the previous studies and the results are shown in Table 11.

TABLE 11

Exploration of the conduction velocity of motor fibers.

| Experimental group | Velocity m/s |
|---|---|
| Diabetic + Saline | 23.62 ± 18.7** |
| Diabetic + Treatment | 54.8 ± 1.66* |
| Non diabetic rats | 64.72 ± 10.55 |

Significant differences between the group of diabetic rats treated with saline and the group of rats receiving the composition of the invention, as well as with the group of non diabetic rats were found (**$p<0.01$ ANOVA and Bonferroni correction). There were also differences between the group treated with EGF containing composition and intact non diabetic animals (* $p<0.05$).

The results demonstrate that three months after diabetes induction there is an increment in the progression of peripheral neuropathy, and a reduction of the conduction velocity of stimuli along motor fibers, particularly when compared with healthy animals. It is important to appreciate, however, that treatment with the pharmaceutical composition set a large difference as compare to the group of diabetic rats receiving saline three times a week during one month. In general, the treatment with the pharmaceutical composition restores motor nervous fibers, improving its conduction capacity.

Another aspect studied is the sensory conduction velocity (SCV), as reflected in Table 12.

TABLE 12

Study of sensitive conduction velocity (SCV).

| Experimental group | Velocity m/s |
|---|---|
| Diabetic + Saline | 31.27 ± 10.6** |
| Diabetic + treatment | 59.42 ± 3.35* |
| Non diabetic rats | 68.9 ± 11.27 |

Significant differences between the group of diabetic rats treated with saline and the group of rats receiving the EGF containing composition, as well as with the group of non diabetic rats were found (**$p<0.01$ ANOVA and Bonferroni correction). There were also differences between the group treated with the composition of the invention and intact non diabetic animals (* $p<0.05$).

The results demonstrate that three months after diabetes induction there is an is increment in the progression of peripheral neuropathy, and a reduction in the conduction velocity of stimuli along sensory fibers, particularly as compared with healthy animals. Deterioration of the parameters is above 50%. It is important to appreciate, however, that treatment with the pharmaceutical composition set a large difference as compare to the group of diabetic rats receiving saline three times a week during one month. In general, the treatment with the pharmaceutical composition restores sensory nervous fibers, which is in agreement with the nociceptive threshold test.

(3) Influence of the Pharmaceutical Composition on the Integrity of Blood Perfusion of a Peripheral Nerve.

The right sciatic nerve of rats was again used as a model. Ten animals per each one of the experimental groups were used. The values from non diabetic rats are included as a reference. The experiment was conducted as previously described, although in this context, the animals were already diabetic for three months and had received sustained treatment for one month with the EGF containing composition or saline according to the experimental group. Results are depicted in Table 13.

TABLE 13

Results of the study conducted with the Laser Doppler Perfusion Imaging System.

| Experimental group | LDPI Units |
|---|---|
| Saline control | 418.5 ± 66.9** |
| Treatment group | 934 ± 60.18* |
| Non diabetic rats | 1397.3 ± 101.55 |

Significant differences between the diabetic group treated with saline and the group receiving the EGF containing composition, as well as with the control group of healthy rats were found (**$p<0.01$ ANOVA with Bonferroni correction) Significant differences (*$p<0.05$) were also found between the group treated with the composition of the invention and intact no diabetic animals.

Treatment with the composition of the invention clearly improved the level of blood perfusion to the nerve. Although values are not comparable yet with those of healthy animals, they are much higher as compared to diabetic rats receiving saline. The molecular mechanism behind this effect has not been clarified yet.

(4) Post-Mortem Determinations and Characterizations.

Histomorphometric Study

One month after conclusion of the treatment with either EGF containing composition or saline, and 120 days after disease induction, animals were sacrificed by an overdose of anesthesia and perfused with saline buffer pH 7.4. A total of ten animals per experimental group were included for histomorphometric studies, and an equivalent number of rats were used for biochemical determinations. In both systems the sciatic nerves from both limbs were dissected. The procedures were similar to those described for the neuropathic damage prevention assay. Samples taken for histological and o histomorphometric studies were stained with hematoxilin/eosin and toluidine blue. At least five fragments of the same nerve were quantitatively studied using MADIP program. The fragments were included in OCT blocks, post-fixed with glutaraldehyde, and sliced horizontal and transversally. The histological indicators assessed have been described above as well as the procedures used for the processing and evaluation:

Total number of blood vessels (in epineural/perineural) in 10 microscopic fields using 10× as constant magnification in longitudinal cuts of the nerve.

Percentage of demyelinated fibers. Evaluated by averaging the values per microscopic field (×20, at least five fields).

Percentage of myelin or non-myelin fibers with lesions (dilated or distorted) per microscopic field (×20, at least five fields).

Percentage of endoneurial collagenization (moderated: 25 to 50%; severe: more than 50% of the endoneurial area in transversal slices, and at least three different sections.

Results are shown in Table 14. Statistically significant differences in the number of blood vessels between both groups of diabetes rats and the intact rats were documented ($p<0.001$). Statistical differences between EGF containing composition treated rats and animals receiving saline were also found ($p<0.05$, ANOVA with Bonferroni correction).

TABLE 14

Morphometric study conducted on fragments of the Sciatic nerve. Evaluation after 30 days.

| Experimental group | No. of blood vessels | % of demyelinated fibers | % of fibers with lesions | % of collagenized area |
|---|---|---|---|---|
| Saline control | 43.2 ± 9.8 | 71.5 ± 22.7 | 83 ± 7.5 | 64.1 ± 16.4 |
| Treatment group | 86.5 ± 14.6 | 50.6 ± 12.3 | 52.6 ± 8.3 | 46.3 ± 9.5 |
| Non diabetic rats | 178.1 ± 44.2 | 0 | 0 | 0 |

The percentages of demyelinated fibers, fibers with lesions and collagenized endoneurial area in diabetic animals were significantly different ($p<0.001$) than the values observed in non diabetic animals. Even though significant differences ($p<0.05$) are detected between healthy animals and those treated with the EGF containing composition, the damage attenuation effect is obvious. The percentages were compared using Fisher exact test.

Partial Conclusions.

The treatment with the composition of the invention, three times per week, during one month, and after the establishment of diabetic neuropathy, reduced significantly the morphological deterioration of the sciatic nerve fibers. Treatment with the composition was also able to reduce the atrophy and degeneration of blood vessels. Again, all these findings are in agreement with the functional tests conducted.

(5) Biochemical Characterization of Nerve Fragments.

Ten animals from each group were used for the biochemical determinations in the is fragments of the sciatic nerve collected. The following biochemical parameters were studied:

Redox Profile:
Total Superoxide Dismutase (tSOD) enzymatic activity total.
Catalase enzymatic activity.
Intra-axonal accumulation of total hydroperoxides (THP).
Intra-axonal accumulation of malonyldialdehyde (MDA).

The results of this study are shown in Table 15.

TABLE 15

Characterization of the Redox state in fragments of sciatic nerve.

| Experimental group | tSOD[a,b] | Catalase | THP[c] | MDA |
|---|---|---|---|---|
| Non diabetic rats | 2108.3 ± 109.7 | 31.8 ± 3.22 | 21.1 ± 1.11 | 0.08 ± 0.005 |
| Diabetic + saline | 375.8 ± 88.2 | 603.6 ± 99.4 | 317.5 ± 12.2 | 0.87 ± 0.1 |
| Diabetic + treatment | 1988.4 ± 101.6 | 86.1 ± 6.5 | 55.8 ± 12.7 | 0.1 ± 0.03 |

Values expressed as the average[a] and the standard deviation[b]. Enzymes expressed as units per milligram of protein per minute.
[c]THP and MDA in nmol/mg of protein.

Statistically significant differences between placebo and treated diabetic animals and the group of rats treated with the EGF containing composition were found ($p<0.01$, two tailed Student t-Test). As shown in Table 15, treatment with the pharmaceutical composition reduces significantly the presence of metabolites indicatives of peroxidation processes in the studied nerve tissue. In parallel, it is shown that treatment attenuates the dysfunction of Superoxide Dismutase enzyme.

(6) Lipoprotein Lipase (LPL) Enzymatic Activity in Sciatic Nerve Fragments.

The aim of this study was to compare the LPL enzymatic activity after one month of treatment with EGF containing composition, as compared to saline treated diabetic animals. Results are shown in Table 16. Significant differences between the diabetic is group treated with saline and the one treated with the composition of the invention were observed (**$p<0.01$, ANOVA and Tukey tests).

TABLE 16

LPL activity in the Sciatic nerve.

| Experimental group | LPL (nmoles AGL/min/g) |
|---|---|
| Non diabetic rats | 7.02 ± 1.24 |
| Diabetic + saline | 2.18 ± 0.73** |
| Diabetic + treatment | 6.29 ± 1.67 |

This analysis demonstrates that treatment with the EGF containing pharmaceutical composition restores LPL enzymatic activity, which consequently improves the capacity of the nerve to synthesized myelin.

Example 3

Demonstration of the Therapeutic Effect of EGF Containing Composition in the Treatment of Patients with Diabetic Neuropathy A total of five patients were treated with the EGF containing composition. Those patients had manifestations of sensory-motor and painful neuropathy, without response to previous treatments. The dose of EGF administered ranged between 20 and 25 µg. The application of the composition containing this active pharmaceutical ingredient was made by infiltration. The treated cases were the following:

Patient PCM.

Fifty years old female patient, with more than 20 years of diagnosis with type 1 Diabetes, manifestations of ischemic cardiopathy, hypertension and nephropathy. A history of sensory-motor neuropathy and manifestations of painful neuropathy, with more than 10 years of evolution and no clinical response to previous treatments. A composition containing 25 µg of EGF and 100 mg of lidocaine per dose was infiltrated in the major sciatic nerve. This procedure was repeated 5 more times for a total of six applications, always in the sciatic nerve, two times a week. After the third infiltration the pain disappeared. Eight weeks after treatment initiation the sensory-motor manifestations ceased, and remain like that through the three months follow up period.

Patient OZD.

Seventy two years old female patient suffering from Diabetes, with severe arterial occlusions and pain at rest. She can not walk and has total leg numbness. Three applications of the same composition were done, in the same anatomic location (major sciatic nerve). The patient referred that leg numbness did not ceased after the administration of EGF containing composition, however, the pain at rest disappeared after the three applications of this composition, and patient could walk faster.

Patient BCB.

Sixty years old female patient, with more than 10 years with a diagnosis of type 1 Diabetes, pain at rest and limbs numbness. She received six applications of the same composition by infiltration in the major sciatic nerve. After the third application the pain disappeared and paresthesias were reduced. Three weeks after the application of the last dose pain reappeared, therefore a new treatment cycle was conducted.

Patient GTC.

Fifty seven years old male patient suffering from Diabetes, with limbs numbness. Six applications of the same composition were done in the same anatomic location, at 4 days intervals. Once concluded the mentioned treatment symptoms of leg numbness disappeared remaining like that through the three months follow up period.

Patient STL.

Sixty eight years old male patient suffering from type I Diabetes for more than 10 years. He shows manifestations of numbness in the lower limbs. Six applications of the same composition were done, in the same anatomic location, at a rate of 2 applications per week. After the first round of treatment (6 doses), lower limbs numbness disappeared to came back after 6 months. A new cycle of treatment was therefore applied, following the same procedures and the manifestations of numbness declined after the third infiltration.

A substantial improvement in the neurological functions of the patients is, in general, observed, with elimination of spontaneous pain at rest and paresthetic sensations.

Example 4

Preparation of the Pharmaceutical Composition Containing PLGA Microspheres with EGF Preparation and Characterization of EGF Loaded Microspheres.

A 5% (w/v) polylactic acid solution (Sigma, St. Louis, Mo., USA) was prepared by dissolving 1 g of the polymer in dichloromethane (DCM)

Three milliliters of the PLGA solution was deposited in a glass container and 100 µl of an aqueous solution of EGF at 30 mg/ml was added.

This mixture was stirred during 2 minutes at 14 000 rpm by means of an Ultraturrax T8 homogenizer, (IKA Labortechnik, Alemania). The resulting emulsion was poured into 30 ml of 1% polyvinyl alcohol and a second emulsion (w/o/w) was obtained through vigorous agitation of the two phases at 14 000 rpm using a T8 Ultraturrax homogenizer (IKA Labortechnik, Germany). The double emulsion was poured into 270 ml of 1% polyvinyl alcohol 30 000-70 000 (Sigma, St. Louis, Mo., USA) and stirred in a homogenizer (IKA Labortechnik, Germany) at 300 rpm during 1 h to evaporate the dichloromethane. Finally, microspheres were collected by filtration, washed 5 times with 50 ml of distilled water and freeze-dried in a lyophilizer (Edwards, UK). Dried microspheres were stored at 4° C. until its use.

The resulting EGF loaded microparticles were spherical and exhibit a regular porous surface (FIG. 1). The yield of the process was 85%, with an encapsulation efficiency ranging between 68 and 71%. The load of the microspheres ranged between 0.82 and 0.85%. The particles were lower than 30 µm.

In Vitro Release of Encapsulated EGF.

Fifty mg of EGF loaded microspheres were suspended in 1 ml of receptor fluid (0.001% Tween 80 and 0.1% sodium azide in PBS pH 7.2). The suspension was incubated at 37° C. under gentle stirring. The samples were centrifuged for 5 min at 5000 rpm in a Hettich microcentrifuge (Tuttlingen, Germany), at days 1, 3, 7, and 14. The supernatant was collected and the same volume of receptor fluid was added. EGF concentration in each sample was assessed by the bicinchoninic acid method to in a microassay format (microBCA assay).

Figure 2:
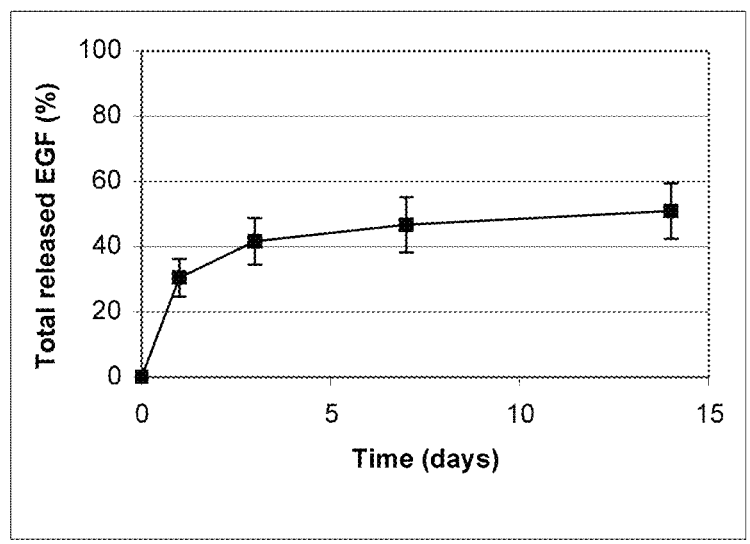
FIG. 2. Release profile of EGF encapsulated in PAL microspheres. Axis X displays time in days and Y axis the amount of EGF released, expressed in percentage of the total amount of EGF within the microspheres used in the assay.

The profile of EGF release from the microspheres exhibited a burst release stage during the first day and a second stage of continuous and gradual EGF release until day 14. Approximately, the 30% of total protein was released during the first stage, while up to the 50% of the EGF contained into the particles was released during the rest of the evaluation period, at an approximate rate of 7 µg per day (FIG. 2).

Example 5

Demonstration of the Therapeutic Effect of an EGF Containing Composition Encapsulated in Microspheres, in Patients with Diabetic Neuropathy Next we summarize some of the characteristics of three patients treated with the composition containing EGF encapsulated in microspheres, and information about the treatment applied to them:

Patient LNP.

Forty seven years old female patient, with more than 10 years with a diagnosis of type 1 Diabetes, with manifestations of sensory-motor and painful neuropathy I. The major sciatic nerve was infiltrated with a composition containing 20 µg of EGF per dose. This procedure was repeated three times for a total of four applications at a frequency of two doses per weeks. Pain was reduced after the third infiltration, and disappeared after the fourth application. Sensory-motor manifestations disappeared two weeks later and remain like that through a three months follow up period.

Patient JVR.

Sixty three years old female patient with type I Diabetes. Exhibit pain at rest and numbness of the limbs. She received six applications of a composition containing 25 µg of EGF per dose, every 12 days. The application of the composition was done by infiltration of the major sciatic nerve. Pain disappeared and paresthesias were reduced after the third application. Six weeks after the last application of the composition pain reappeared and therefore a new round of treatment was initiated.

Patient DGR.

Fifty two years old male patient with type Diabetes, suffering from limbs numbness. He received five doses of the above described composition containing EGF encapsulated in microspheres for the slow release, in the same anatomic site, and at 14 days intervals. Once concluded the EGF treatment the legs numbness had already disappeared, remaining like that through the four months follow up period.

The invention claimed is:

1. A method for the morphofunctional restoration of peripheral nerves in a mammal having diabetic neuropathy, said method comprising administering by infiltration to the periphery of nerve trunks and/or ganglia a composition comprising Epidermal Growth Factor (EGF).

2. The method according to claim 1, wherein said diabetic neuropathy is painful sensory-motor neuropathy.

3. The method according to claim 2, wherein said painful sensory-motor neuropathy affects the lower limbs.

4. The method according to claim 1, wherein said EGF is human recombinant EGF.

5. The method according to claim 1, wherein said EGF is encapsulated in microspheres.

6. The method according to claim 1, wherein said composition is liquid or lyophilized to be reconstituted before its use.

7. The method according to claim 6, wherein said composition is an aqueous composition, optionally buffered, or a lyophilized composition to be reconstituted with water, or with an aqueous buffer solution.

8. The method according to claim 1, wherein said composition contains from 10 to 1000 micrograms of EGF/milliliter.

\* \* \* \* \*

UNITED STATES PATENT AND TRADEMARK OFFICE
CERTIFICATE OF CORRECTION

| | | |
|---|---|---|
| PATENT NO. | : 9,034,826 B2 | Page 1 of 1 |
| APPLICATION NO. | : 14/140849 | |
| DATED | : May 19, 2015 | |
| INVENTOR(S) | : Fernandez Montequin et al. | |

It is certified that error appears in the above-identified patent and that said Letters Patent is hereby corrected as shown below:

In the specification

Column 1, line 37

Now reads: "the is nervous fibers"
Should read: -- the nervous fibers --

Column 4, line 14

Now reads: "ischemic to neuritis"
Should read: -- ischemic neuritis --

Signed and Sealed this
Twenty-ninth Day of December, 2015

Michelle K. Lee
*Director of the United States Patent and Trademark Office*